(12) United States Patent
Lee et al.

(10) Patent No.: US 8,524,888 B2
(45) Date of Patent: Sep. 3, 2013

(54) METHOD OF PRODUCING D-PSICOSE CRYSTALS

(75) Inventors: Kang Pyo Lee, Seoul (KR); Sang Hoon Song, Suwon-si (KR); Seung Won Park, Yongin-si (KR); Sung Bo Kim, Seoul (KR); Young Ho Hong, Gwangmyeong-si (KR); Joo Hang Lee, Ansan-si (KR); Taek Beom Kim, Seoul (KR); Jun Gap An, Ansan-si (KR); Jung Hoon Kim, Seoul (KR)

(73) Assignee: CJ Cheiljedang Corp. (KR)

( * ) Notice: Subject to any disclaimer, the term of this patent is extended or adjusted under 35 U.S.C. 154(b) by 227 days.

(21) Appl. No.: 13/053,435

(22) Filed: Mar. 22, 2011

(65) Prior Publication Data

US 2011/0237790 A1 Sep. 29, 2011

(30) Foreign Application Priority Data

Mar. 26, 2010 (KR) ........................ 10-2010-0027546

(51) Int. Cl.
*C07H 1/06* (2006.01)
*C07H 1/08* (2006.01)

(52) U.S. Cl.
USPC ........................................................ 536/127

(58) Field of Classification Search
None
See application file for complete search history.

(56) References Cited

U.S. PATENT DOCUMENTS

| 3,928,062 A | 12/1975 | Yamauchi |
| 2009/0068710 A1 | 3/2009 | Izumori et al. |

FOREIGN PATENT DOCUMENTS

| CN | 101294176 A | 10/2008 |
| EP | 0225503 A1 | 6/1987 |
| JP | P1974-102853 | 9/1974 |
| JP | 03228687 A | 10/1991 |
| JP | 1991228687 A | 10/1991 |
| JP | 2001354690 A | 12/2001 |
| KR | 0141981 B1 | 3/1998 |
| WO | 9006317 A1 | 6/1990 |

OTHER PUBLICATIONS

Itoh et al. Journal of Fermentation and Bioengineering vol. 80, No. 1, 101-103, 1995.*
Barrett et al. Solubility Curve and Metastable zone Width using Lasentec FBRM & PVM, Lansentec Users Forum, Charlston, 2002.*
Notice of Allowance with English Translation of front page for Korean Application No. 10-2010-0027546 dated Sep. 28, 2012.
Matsuo, et al., D-Psicose, a rare sugar that provides no energy and additionally beneficial effects for clinical nutrition, Asia Pacific Journal of Clinical Nutrition (2004) 13 (Suppl) p. S127.
Takeshita, et al., Mass Production of D-Psicose from D-Fructose by a Continuous Bioreactor System Using Immobilized D-Tagatose 3-Epimerase, Journal of Bioscience and Bioengineering vol. 90, No. 4, pp. 453-455, 2000.
Matsuo, et al., Dietary D-psicose, a C-3 epimer of D-fructose, suppresses the activity of hepatic lipogenic enzymes in rats, Asia Pacific Journal Clinical Nutrition (2001) 10(3): pp. 233-237.
Chinese Office Action with English Translation for Application No. 201110129821.1 dated Apr. 22, 2013.
Japanese Office Action with English Translation for Application No. 2011-066870 dated Jul. 8, 2013.
Izumori, "Production of Rare Sugar by Bacteria and Enzyme Reaction", Cited Document 2, pp. 5-8, Jul. 8, 2007.
Izumori, "Enzyme Production of Rare Sugar D-psicose", Cited Document 3, Bio Industry, pp. 34-39, vol. 19, No. 5, May 2002.
Itoh, et al., "Preparation of D-Psicose from D-Fructose by Immobilized D-Tagatose 3-Epimerase", Journal of Fermentation and BioEngineering, Cited Document 6, vol. 80, No. 1, pp. 101-103 1995.
Beveridge, et al., "The preparation of decagram quantities of D-psicose by the isomerization of D-fructose, and separation of the products on a calcium-ion cation-exchange resin", Carbohydrate Research, Cited Document 7, 101 (1982) pp. 348-349.
Izumori, "Enzyme Synthesis of Rare Sugar D-psicose", Cited Document 1, pp. 160-166 Oct. 10, 2001.

* cited by examiner

*Primary Examiner* — Layla Bland
(74) *Attorney, Agent, or Firm* — Cantor Colburn LLP

(57) ABSTRACT

The present invention relates to a method of producing D-psicose crystals from a D-psicose solution by using supersaturation.

7 Claims, 3 Drawing Sheets

2

METHOD OF PRODUCING D-PSICOSE CRYSTALS

CROSS-REFERENCE TO RELATED PATENT APPLICATION

This application claims the benefit of Korean Patent Application No. 10-2010-0027546, filed on Mar. 26, 2010, in the Korean Intellectual Property Office, the disclosure of which is incorporated herein in its entirety by reference.

BACKGROUND OF THE INVENTION

1. Field of the Invention

The present invention relates to a method of producing D-psicose crystals from a D-psicose solution by using supersaturation.

2. Description of the Related Art

D-psicose is a natural sugar present in a trace amount in isomerization of molasses or glucose and a monosaccharide with a sweetness of about 70% relative to sugar. It has been reported that D-psicose is a sweetener that has little effect on body weight increase because it is not metabolized by humans, has substantially no calories, and inhibits the formation of body fat (Matuo, T. et. Al., *Asia Pac. J. Clin. Nutr.*, 10, 233-237, 2001; Matsuo, T. and K. Izumori, *Asia Pac. J. Clin. Nutr.*, 13, S127, 2004).

Recently, effects of D-psicose on non-carious and anti-carious functions have been reported, and thus development of D-psicose, as a material which aids in teeth health and as a sweetener which may replace sugar, has been actively performed.

Although D-psicose has attracted attention from the food industry as a sweetener to prevent an increase in body weight due to its properties and functionalities, only a trace amount of D-psicose is produced from fructose at high temperatures, and thus it is difficult to produce D-psicose via chemical synthesis. Although mass production methods by reacting fructose with D-tagatose epimerase or reacting fructose with D-psicose epimerase have been reported, the yields of D-psicose are so low that production costs thereof are high.

Recently, the present inventors have reported a method of economically producing D-psicose by isomerizing glucose to fructose, followed by a reaction of fructose with immobilized cells which produces D-psicose epimerase (Korea Patent Application No. 10-2009-0118465).

Reaction solutions containing D-psicose produced by enzymatic reactions are low-purity products that contain D-psicose in solid form in an amount of about 20% to about 30% by weight, and thus it is required to isolate D-psicose at high purity. Various methods are applied to materials that are industrially produced to isolate them at high purity. In the case of sugars, chromatography is usually used to prepare a highly pure liquid, followed by crystallization to obtain high-purity sugar product. For D-psicose, an industrially applicable method of production is yet to be developed.

A method of preparing D-psicose in a powder form by removing unreacted fructose in a D-psicose reaction solution via yeast fermentation and using a large amount of ethanol was reported (Kei T. et. al., *J. Biosci. Bioeng.*, 90(4), 453-455, 2000). However, the use of ethanol in large amounts requires expensive facilities for explosion proofness and recovery of products, and problems, such as stirrer failure caused by the use of organic solvents and presence of foreign materials in recovered products, can occur. In addition, because the final products are in the form of fine powders, they may be lost in large quantities during dehydration, washing, and drying processes. While D-psicose is powdered to produce final products, the powders are adsorbed to each other, which introduces impurities among the powder particles, thereby lowering the purity of the final product. For the products in the form of fine powders, the increase in volume is larger than the increase in weigh, which leads to increase in manufacturing costs due to high volume packaging and additional costs in the distribution. In addition, such products in fine chemicals are disadvantageous in food manufacturing process due to low flowability. Therefore, there still remains a need for a method of producing pure D-psicose, in the form of crystals rather than fine powders, in order to economically produce D-psicose without using organic solvents such as ethanol and improve flowability in the manufacturing process and product value.

BRIEF DESCRIPTION OF THE DRAWINGS

The above and other features and advantages of the present invention will become more apparent by describing in detail exemplary embodiments thereof with reference to the attached drawings in which.

SUMMARY OF THE INVENTION

Figure 1:
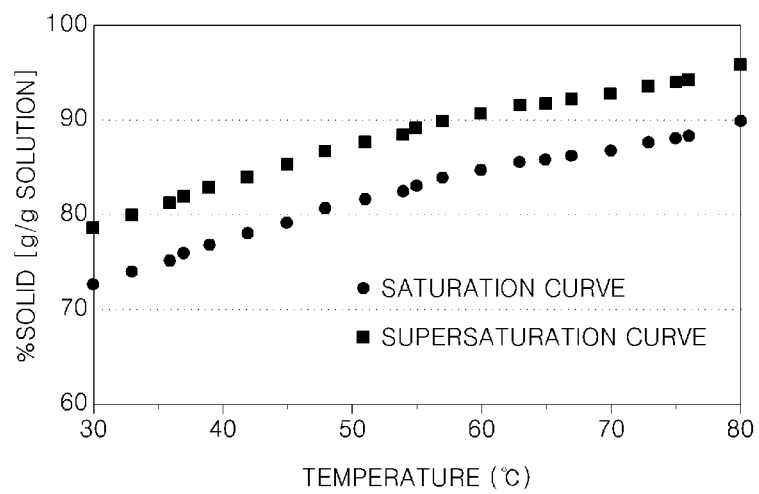
FIG. 1 is a graph illustrating a saturation curve and a supersaturation curve of pure D-psicose in relation to temperature.

Thus, the present inventors have conducted studies on a method of producing D-psicose crystals from a D-psicose solution obtained by biological conversion or enzymatic reactions without using an organic solvent, wherein the D-psicose crystals are produced in appropriate sizes by maintaining the D-psicose solution in a supersaturated state under a metastable zone, thereby leading to completion of the present invention.

The present invention provides a method of producing D-psicose crystals by maintaining a D-psicose solution in a metastable zone present between a saturation curve and a supersaturation curve.

DETAILED DESCRIPTION OF THE INVENTION

According to an aspect of the present invention, there is provided a method of producing purified D-psicose crystals, including:

removing impurities from a D-psicose solution to obtain a purified D-psicose solution;

concentrating the purified D-psicose solution; and crystallizing D-psicose from the concentrated D-psicose solution in a supersaturated state under a metastable zone.

As used herein, the term "supersaturated state" refers to an unstable state in which a solute is dissolved beyond the dissolution capacity of a solvent and a state in which the solute may be crystallized into a solid. Thus, a supersaturated state should be reached in a solution in order to separate a solute from the solution by crystallization. In general, the supersaturated state of a solution may be affected by external conditions, impurities, temperature, concentration, pH levels, and the like.

As used herein, the term the supersaturated state under a "metastable zone" refers to a range from equilibrium concentration, that is, saturation concentration to a minimum supersaturation concentration on which crystals are spontaneously formed. Crystallization such as crystal nucleation does not occur at concentrations in this range. However, when crystals are added from outside to a solution of a concentration in this range, crystal growth spontaneously occurs and the crystal size increases because the amount of the solute in the solution is at a supersaturation concentration. That is, when seeds are introduced into a solution at a saturated concentration or higher in order to produce crystals, the seeds grow in a metastable zone to form crystals. When a solution for crystallization is excessively concentrated or rapidly cooled down, it reaches a supersaturated state exceeding a metastable zone, and thus crystal nucleation, rather than crystal growth, occurs to form a plurality of fine crystals. Thus, in order to obtain appropriate sized crystals, crystallization should be performed at an appropriate rate while a solution for crystallization is maintained in a supersaturated state under a metastable zone.

In an embodiment of the present invention, a D-psicose solution as a starting material may be prepared by bacteria from *Corynebacterium* genus expressing a D-psicose epimerase or by a D-psicose epimerase isolated therefrom.

In an embodiment of the present invention, as described in Korea Patent Application No. 2009-0118465, a D-psicose solution may be obtained by immobilizing cells obtained by culturing *Corynebacterium glutamicum* KCTC 13032 or an enzyme isolated therefrom in an immobilized carrier and supplying to the immobilized cells or enzyme fructose as a substrate.

In order to obtain D-psicose crystals from a D-psicose solution, other materials that may affect the purification and crystallization of D-psicose should be removed to form a condition required for efficient crystallization.

Therefore, a method of producing D-psicose crystals according to the present invention may include removing impurities from a D-psicose solution to obtain a purified D-psicose solution.

In an embodiment of the present invention, the obtaining of the D-psicose solution may include:

passing the D-psicose solution through a column filled with decolorants to decolor the D-psicose solution;

desalting the decolored D-psicose solution by ion exchange chromatography; and passing the desalted D-psicose solution through a column filled with ion exchange resins to which a calcium active group is attached to obtain a purified D-psicose solution.

In an embodiment of the present invention, the desalting of the D-psicose solution may be performed by chromatography in which the solution is passed through a column filled with a cation exchange resin, a column filled with an anion exchange resin, and a column filled with a mixture of a cation exchange resin and an anion exchange resin.

In general, isolation by chromatography is used in order to obtain high-purity D-psicose. In order to obtain D-psicose crystals, the amount of D-psicose in a D-psicose solution should be about 70% to about 85% or more. Accordingly, D-psicose should be purified and concentrated to a desired level before crystallization because the purity of D-psicose in a D-psicose solution prepared by a D-psicose epimerase reaction is about 22%, which is too low to perfume crystallization directly. In order to obtain high-purity D-psicose crystals, impurities may be removed by decoloring and desalting the solution and D-psicose may be purified by chromatography, for example, chromatography in a column filled with an ion exchange resin to which a calcium active group is attached prior to crystallization.

A method of producing D-psicose crystals according to the present invention may include concentrating a purified D-psicose solution.

In an embodiment of the present invention, the concentrating of the purified D-psicose solution may be performed at about 60° C. to about 70° C. When the temperature of the concentrated solution is increased to higher than about 70° C., D-psicose may be thermally denatured. When the temperature is decreased to lower than about 60° C., it is difficult to concentrate the solution to a desired level. Since the temperature of a reactant rapidly increases by heat of evaporation as the concentrating proceeds, concentration of a solution should be conducted rapidly while maintaining the temperature at about 70° C. or less.

In an embodiment of the present invention, the concentrating of the D-psicose solution may be performed at about 65° C. or less.

A method of producing D-psicose crystals according to the present invention may include crystallizing D-psicose from the concentrated D-psicose solution in a supersaturated state under a metastable zone by controlling the temperature and concentration of the solution.

In an embodiment of the present invention, the concentrated D-psicose solution used in the crystallizing may be a D-psicose solution of about 70% to about 85% (g/g) or more.

In an embodiment of the present invention, D-psicose seeds may be added to the concentrated D-psicose solution used in the crystallizing in an amount of about 0.01% to about 1% (g/g) based on a total amount of D-psicose in the D-psicose solution.

In the present invention, D-psicose crystals are produced by maintaining a D-psicose solution in a supersaturated state under a metastable zone, where D-psicose is present above or at an equilibrium concentration in which D-psicose forms an equilibrium state with a solvent in a solution and crystal growth simultaneously occurs. The supersaturated state required for crystallization may be maintained by lowering the temperature of a D-psicose solution or changing the concentration of D-psicose in the D-psicose solution.

In an embodiment of the present invention, a progress of crystallization in the crystallizing may be monitored by collecting a sample at a predetermined interval to observe the sample with the naked eye or by using a microscope or analyzing a sugar concentration in a supernatant obtained by centrifugation of the sample. In accordance with the result, the temperature or concentration of D-psicose may be controlled.

In an embodiment of the present invention, a supersaturated state under a metastable zone of the D-psicose solution in the crystallizing may be maintained by decreasing the temperature when the crystal growth of D-psicose stops in the solution or the concentration of the D-psicose solution does not change any more after adding D-psicose seeds are added to the D-psicose solution.

In an embodiment of the present invention, a supersaturated state under a metastable zone of the D-psicose solution in the crystallizing may be maintained by adding a D-psicose solution at a concentration lower than that of the D-psicose solution when D-psicose is concentrated to a level of supersaturation or higher, following addition of D-psicose seeds to the D-psicose solution and crystal growth with gentle stirring of the solution, for example, stirring at about 10 rpm.

In an embodiment of the present invention, a D-psicose solution to be added to maintain the D-psicose solution in a supersaturated state under a metastable zone in the crystallizing includes D-psicose at a concentration lower than that of the D-psicose solution concentrated to a level of supersaturation or higher. For example, the D-psicose solution to be added may be a D-psicose solution of about 60% to about 70%.

In an embodiment of the present invention, a supersaturated state in the crystallizing may be present between a saturation concentration and a concentration higher than the saturation concentration by about 6% (g/g solution).

A supersaturation concentration is an intrinsic property of a material and may be obtained by cooling down or concentrating a saturated solution. The supersaturation concentration and the supersaturation temperature may be defined, respectively, as a concentration and a temperature, at which a highly concentrated solution reaches an unstable state to start form fine crystals, when the temperature of the solution is slowly reduced from the temperature at which it reaches its saturation. A supersaturation concentration at which crystallites are generated may be identified by adding deionized water to a solution of a supersaturation concentration, reheating the solution to dissolve crystallites rapidly, controlling the temperature of the solution to a saturation temperature at a diluted concentration, and recooling the solution. A metastable zone of a material may be identified by repeating the dilution, heating, and recooling of solutions of the material at various saturation concentrations. D-psicose also has a concentration range for its inherent metastable zone and the range is identified to be from a saturation concentration or higher to about 6% higher than the saturated concentration. Crystallization may be performed to obtain crystals which are stable in shape and large in size, while maintaining the D-psicose solution in a metastable zone of D-psicose.

In an embodiment of the present invention, a method of producing D-psicose crystals according to the present invention may further include:

recovering D-psicose crystals obtained in the crystallizing, washing the crystals with deionized water, and drying the crystals.

The drying of the crystals may be performed in a fluidized bed dryer or a vacuum dryer.

In an embodiment of the present invention, the purified D-psicose crystals have a size of about 0.1 mm to about 0.2 mm.

In an embodiment of the present invention, the purified D-psicose crystals may be produced by a method including:

concentrating a D-psicose solution produced by enzymatic reactions and the like to a concentration of about 40% (g/g solution) to pass the resulting solution through a column filled with granulated active carbon (GAC) decolorants at a linear velocity of about 4 m per 1 hours for decoloration;

injecting the decolored D-psicose solution into columns each of which is filled with a cation exchange resin, an anion exchange resin, and a mixture of a cation exchange resin and an anion exchange resin at about 40° C. at a speed twice the volume of the ion exchange resins per hour so as to desalt the decolored D-psicose solution;

concentrating the D-psicose solution purified by decoloring and desalting, to a concentration of about 60% (g/g solution) and passing the solution through a separation column filled with an ion exchange resin, to which a calcium active group is attached, to separate psicose from fructose;

concentrating the separated D-psicose solution to a concentration of about 85% (g/g) at about 70° C. or lower in a concentrator;

injecting into the concentrated D-psicose solution D-psicose seeds in an amount of about 0.01% to about 1% (g/g) based on a total amount of D-psicose dissolved in the concentrated D-psicose solution and controlling temperature and concentration to crystallize D-psicose from the solution in a supersaturated state under a metastable zone; and separating D-psicose crystals by centrifugation from the solution subject to the crystallization, washing the solution and the D-psicose crystals, and drying the crystals on a fluidized bed dryer or a vacuum dryer.

Hereinafter, the present invention will be described in detail with reference to specific examples. However, these examples are only for illustrative purposes, and the scope of the present invention is not limited to these examples.

Example 1

Production of a Low-Purity D-Psicose Solution by Using a Microorganism of *Corynebacterium* Genus As disclosed in Korea Patent Application No. 10-2009-0118465, D-psicose was prepared by employing a method of continuously producing D-psicose, including culturing *Corynebacterium glutamicum* KCTC 13032 and converting fructose into D-psicose by carriers on which the micro-organism or a D-psicose epimerase isolated therefrom were immobilized. The level of D-psicose in a D-psicose solution prepared by employing this method was about 22%, which was too low to conduct direct crystallization therefrom.

Example 2

Purification of a Low-Purity D-Psicose Solution

The D-psicose solution produced in Example 1 was concentrated to about 40% (g/g solution), followed by passage through a decolorization column filled with granulated active carbon to remove colored materials in the concentrated solution.

The purity of D-psicose in the D-psicose solution produced in Example 1 was about 22% as the solid content, which was so low that it was not appropriate for crystallization. The purity of a material to be crystallized should be increased to about 70% to about 90% or more for crystallization. For efficient isolation of D-psicose by chromatography, ions should be removed from a D-psicose solution. When an ionic component is present in a solution to be separated, an active group in a separation resin is substituted by the ionic component, reducing the separation capability of the resin and thus it is impossible to use the separation resin repetitively. Accordingly, the decolored D-psicose solution prepared above was passed through a column filled with a cation exchange resin substituted by a hydrogen group and an anion exchange resin substituted by a hydroxyl group, followed by passage through an ion exchange column filled with a mixture of a cation exchange resin and an anion exchange resin in a final step to remove the ionic components in the solution. Removal of the ionic components in the solution was confirmed by measurement of electric conductivity using conductometer. The electric conductivity of the purified solution was controlled to be about 10 microsiemens/cm or less.

Example 3

Preparation of a Highly Pure D-Psicose Solution by Chromatography

The low-purity D-psicose solution from which impurities such as colored materials and the ionic component had been removed by decoloration and desalting in Example 2 was concentrated up to about 60% (g/g solution), followed by passage through an ion exchange resin (Purolite PCR 642 K) substituted by a calcium group to obtain a purified D-psicose solution.

The volume of the ion exchange resins which filled the ion exchange resin column was about 200 l, the volume of a sample to be passed through the column, that is, a purified D-psicose solution prepared in Example 2, was about 20 l, and the operation temperature was about 60° C. The sample was injected and eluted with deionized water at about 260 l/hr, and then concentrations of fructose and D-psicose were respectively measured by using a HPLC system (HP, Agilent 1200 series) in each fraction collected. A pure D-psicose fraction was obtained and a fraction containing D-psicose and fructose was concentrated and again used as a sample to be separated. A column (Bio-Rad, Inc.) substituted by a calcium group was used for a HPLC analytical column, and deionized water was applied at a flow rate of about 0.5 ml/min.

Example 4

Concentration of a D-Psicose Solution

Figure 2:
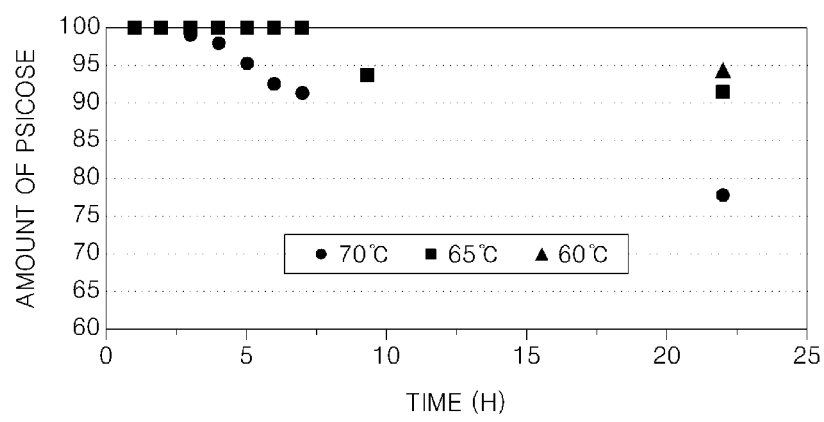
FIG. 2 is a graph illustrating residual amounts of D-psicose at a concentration of 80% (g/g solution) in relation to temperature.

In order to obtain a D-psicose concentrate required for crystallization, the D-psicose solution purified in Example 3 was put into a vacuum concentrator (EYELA Inc., N-11) and concentrated to about 80% (g/g solution). The concentrated solution was aliquoted into each tube, which was allowed to stand in water baths at 70° C., 65° C., and 60° C., respectively. Samples were collected at a regular interval over time to measure residual amounts in the aliquots of the concentrated solution. The results are shown in FIG. 2. When the temperature of the concentrated solution was higher than about 70° C., it was identified that D-psicose was thermally denatured after 3 hours and only about 78% relative to an initial amount remained after 22 hours. Although the internal temperature was maintained at about 40° C. or less by heat of evaporation in the concentration process, the temperature rapidly increased when the amount of D-psicose became about 80% (g/g solution) or more. From these results, it was identified that when D-psicose is concentrated to about 80% (g/g solution) or more, it is necessary to rapidly decrease the internal temperature of the concentrate to about 70° C. or less, or to perform the concentration step, for example, at about 65° C. or less.

Example 5

Preparation of D-Psicose Seeds

Figure 3:
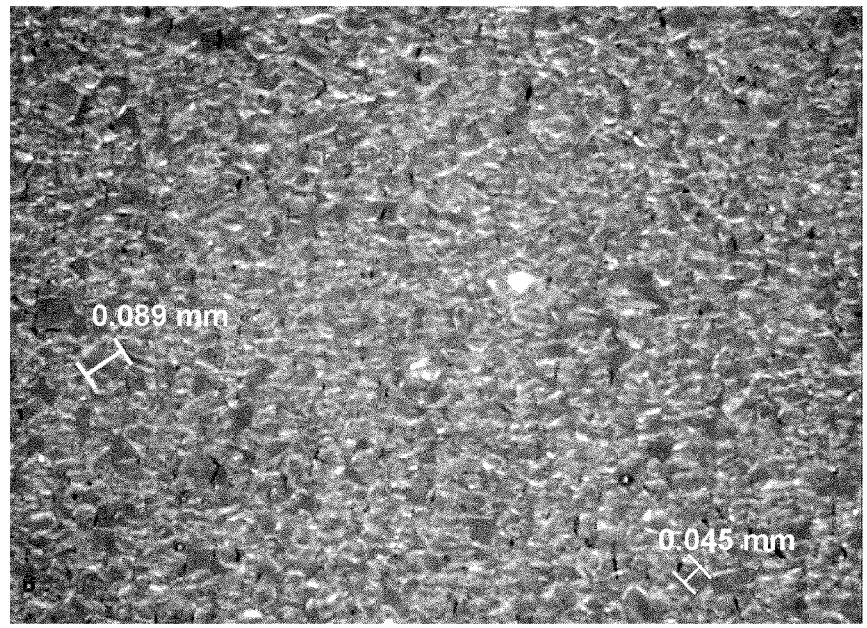
FIG. 3 is a photo showing produced D-psicose seeds observed using a microscope.

The D-psicose solution (containing about 1000 g of D-psicose) purified and separated in Example 3 was concentrated to about 85% (g/g solution) as described in Example 4. 1 g of a 95% purity product (Sigma) was purchased, put into a mortar, ground, and then mixed with an ethanol solution. A reactor system (IKA®, LR-2. ST) equipped with a double jacketed 2 l reaction bath was used as a crystallizer, the initial temperature of a concentrated solution in the crystallizer was controlled to about 50° C., a 95% purity D-psicose ethanol solution prepared was added as a seed, and the resulting solution was stirred at a speed of about 100 rpm. After confirming the mixing of the concentrated solution and the seeds, the stirring speed was recontrolled to about 10 rpm and the mixture was cooled down at about 1° C./hour. A microscope was used to determine a concentration at which the number of D-psicose crystals rapidly increase. This state was deemed as a supersaturation. Subsequently, the temperature was maintained to grow the crystals until microscopic observation and saccharimetric analysis showed that crystals did not grow any more or the sugar concentration of a supernatant did not change any more and then the temperature of the solution was cooled down by about 1° C. After the temperature was cooled down to about 33° C., a final crystal state was obtained, which is shown in FIG. 3. The cooling was stopped at about 33° C., and dehydration by centrifugation, washing, and drying were performed to obtain D-psicose seeds. The final seeds obtained were in a range from about 0.04 mm to about 0.10 mm in diameter, and the dry weight was about 40% relative to the weight of D-psicose present in the initial aqueous solution.

Example 6

Determination of a Saturation Concentration and a Supersaturation Concentration of D-Psicose The procedures in Examples 3 to 5 were repeated to obtain a pure D-psicose. The D-psicose prepared was dissolved to obtain a saturation curve over temperature. Starting at 30° C., a concentration at which D-psicose was not dissolved any more when adding a small amount of D-psicose was defined as a saturation concentration at the corresponding temperature, and the saturation concentrations were determined by increasing the temperature to 80° C. to formulate a D-psicose saturation curve shown in FIG. 1.

In addition, D-psicose was dissolved and concentrated to about 85% (g/g solution). Subsequently, the D-psicose solution was put into a crystallizer and slowly cooled down to a temperature at which fine crystals were rapidly formed. Deionized water was added to change the saturation concentration, and then the cooling-down experiment was repeated to determine supersaturation concentration for respective saturation temperatures. Based on the results, a D-psicose supersaturation curve shown in FIG. 1 was prepared.

Example 7

Crystallization of D-Psicose by Using Temperature Changes

A D-psicose solution (containing about 2,780 g of D-psicose) purified as described in Example 3 was obtained, concentrated to about 85% (g/g solution), and put into a crystallizer. The crystallizer was controlled to maintain the temperature at about 50° C. The seeds obtained in Example 5 were put into a mortar and mixed with ethanol to prepare a D-psicose solution. The D-psicose ethanol solution was introduced as a seed to the concentrated D-psicose solution in the crystallizer such that the seeds are present at an amount of 0.3% (w/w) relative to D-psicose in the solution for crystallization. Subsequently, the resulting solution was stirred by a stirrer at about 100 rpm to allow the seeds to be uniformly distributed in the concentrated solution. Then, the speed of the stirrer was decreased to about 10 rpm, samples were collected at a predetermined interval over time to observe by microscope an increase in the number of crystals and a change in crystal size. The samples centrifuged by using 1.5 ml microtubes and the concentration and purity of supernatants were measured by a saccharimeter, and HPLC, respectively.

When the temperature reached a point (saturation temperature) at which a change in crystal size or a change in concentration of a supernatant did not occur any more, the temperature of the crystallizer was cooled down by about 1° C. so that the D-psicose solution would exist in a zone between its saturation concentration and its supersaturation concentration, that is, a supersaturated state under a metastable zone be maintained.

When a D-psicose solution for crystallization was shifted to a supersaturation zone by rapid cooling, fine crystals started to be formed and the amount of seeds was increased, finally leading to a reduction in crystal size. When the crystal size is small, it is not easy to perform dehydration by centrifugation, thereby making it difficult to apply the crystals in real processes.

Figure 4:
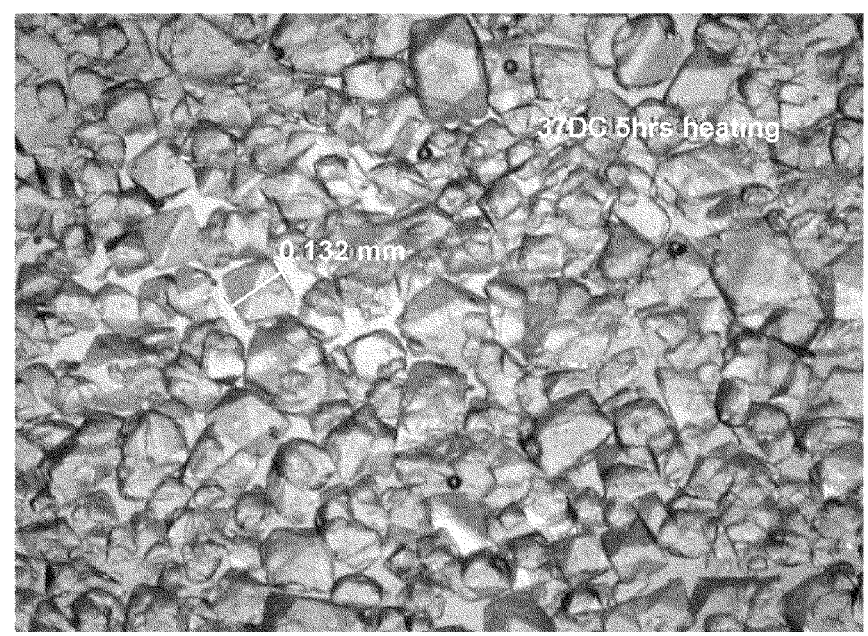
FIG. 4 is a photo showing D-psicose crystals produced by temperature control according to an exemplary embodiment of the present invention, which was captured using a microscope.
Figure 5:
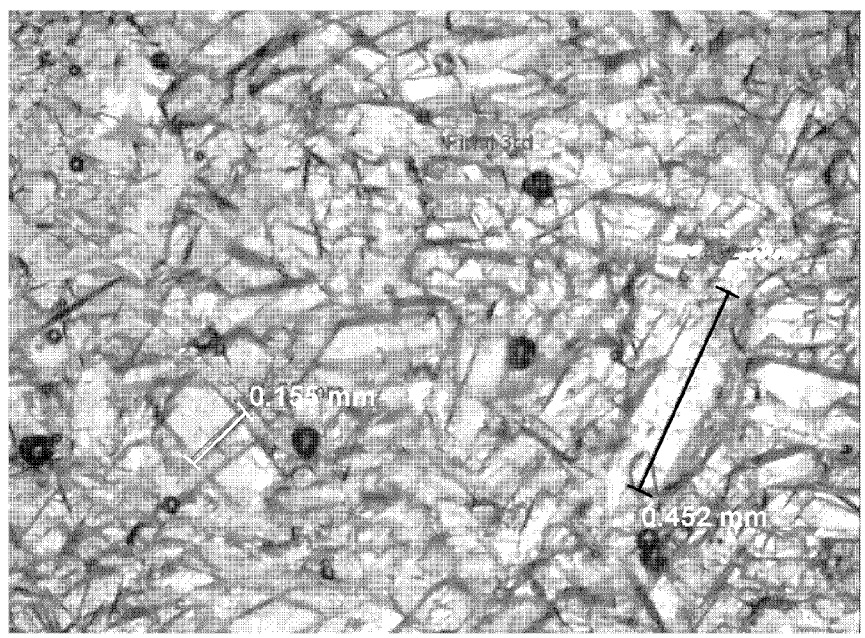
FIG. 5 is a photo showing D-psicose crystals produced by vacuum concentration according to an exemplary embodiment of the present invention, which was captured by using a microscope.

The final supernatant was cooled down until the concentration reached about 74% (g/g solution), and the crystal state at the time is shown in FIG. 4. A solution in which the crystallization had been completed was put into a high-speed centrifugal dehydrator and centrifuged at about 4,000 rpm for about 10 minutes to decant a supernatant and recover only crystals. Subsequently, deionized water was added in the form of spray during dehydration to wash out a supernatant from external surfaces of the crystals. D-psicose recovered after the dehydration was transferred to a fluidized bed dryer or a vacuum dryer for drying. Result showed that the amount of D-psicose crystals after the drying was about 1,408 g, about 50% recovery compared to about 2,789 g of D-psicose which had been initially dissolved. The crystal size ranged between about 0.1 mm and about 0.2 mm, corresponding to about ½ of the sizes of commercially available fructose or sucrose.

Example 8

Crystallization of D-Psicose by Using Concentration Changes

About 5,000 g in solid content were obtained from a D-psicose solution purified as described in Example 3. Out of them, about ⅔ was concentrated to about 60% (g/g solution) and the remaining ⅓ was concentrated to about 80% (g/g solution). The concentrated solution of 80% (g/g solution) was put into a concentrator (EYELA Inc., N-11) equipped with a 10 l flask and concentrated while stirring at about 10 rpm. A D-psicose ethanol solution prepared in Example 5 as seeds was added to the flask under vacuum, and a thermometer was installed in the flask to measure a change in internal temperature. As the concentration proceeded, crystals grew. Samples were collected at a predetermined interval over time to observe by microscope an increase in the number of crystals and a change in crystal size, and 1.5 ml microtubes were used for centrifugation, followed by measurement of the concentration of a supernatant by a saccharimeter and measurement of the purity of the supernatant by HPLC. The solution was sometimes concentrated to a level of supersaturation or higher, thereby leading to formation of fine crystals. As a result, the crystal size was decreased. In this case, a previously prepared D-psicose solution at a low concentration of about 60% (g/g solution) was injected to dissolve the fine crystals produced and simultaneously increase the purity of the concentrated solution for crystallization, whose purity had been decreased due to the growth of crystals.

Samples were collected and subjected to centrifugation. Subsequently, when a change in crystal size was not observed any more, the vacuum was removed and the samples were allowed to stand at about 40° C. for about 12 hours. The crystal state at the time is shown in FIG. 4. A solution in which the crystallization had been completed was put into a high-speed centrifugal dehydrator and centrifuged at about 4,000 rpm for about 10 minutes to decant a supernatant and recover only crystals. Subsequently, deionized water was added in the form of spray to wash out a supernatant on external surfaces of the crystals. D-psicose crystals recovered after the dehydration were transferred to a fluidized bed dryer or a vacuum dryer for drying. It was observed that the amount of crystals after the drying was about 2,650 g, about 53% recovery compared to about 5,000 g of D-psicose which had been dissolved. It was determined that the crystal size ranged between about 0.1 mm and about 0.2 mm. When the crystals were compared with crystals prepared by using changes in temperature, the length of the crystals thus obtained were longer than those obtained by changes in temperature.

ADVANTAGEOUS EFFECT

A production method according to an embodiment of the present invention may be used to produce D-psicose crystals, which are pure and appropriate for industrial applications, from a D-psicose solution through economical crystallization processes which do not use organic solvents.

Although exemplary embodiments of the present invention have been described, it should be understood that the embodiments described above are provided only as examples in all aspects and do not limit modifications and variations of the invention. The scope of the invention is specified by the appended claims rather than the detailed description given above. It should be interpreted that the spirit and the scope of the claims and all the modifications or variations derived from their equivalents belong to the scope of the invention.

What is claimed is:

1. A method of producing D-psicose crystals, the method comprising:
   removing impurities from a D-psicose solution to obtain a purified D-psicose solution;
   concentrating the purified D-psicose solution; and
   crystallizing D-psicose from the concentrated D-psicose solution in a supersaturated state under a metastable zone in the absence of organic solvent,
   wherein the concentrating of the purified D-psicose solution is performed at a temperature of about 60° C. to about 70° C.

2. The method of claim 1, wherein the obtaining of the purified D-psicose solution includes:
   passing the D-psicose solution through a column filled with decolorants to decolor the D-psicose solution;
   desalting the decolored D-psicose solution by ion exchange chromatography; and
   passing the desalted D-psicose solution through a column filled with ion exchange resins to which a calcium active group is attached to obtain a purified D-psicose solution.

3. The method of claim 1, wherein the crystallizing D-psicose from the concentrated D-psicose solution comprises adding D-psicose seeds to the concentrated D-psicose solution in an amount of about 0.01% to about 1% (g/g) based on a total amount of D-psicose in the concentrated D-psicose solution.

4. The method of claim 1, wherein the concentrated D-psicose solution used in the crystallizing is a D-psicose solution of about 70% (g/g) or more.

5. The method of claim 1, wherein the crystallizing D-psicose from the concentrated D-psicose solution comprises monitoring a progress of crystallization in the crystallizing to maintain the concentrated D-psicose solution in a supersaturated state under a metastable zone by decreasing the temperature of the solution when a crystal growth of D-psicose stops or a concentration of the D-psicose solution does not change any more.

6. The method of claim 1, wherein the crystallizing D-psicose from the concentrated D-psicose solution comprises monitoring crystallization progress in the crystallizing to maintain the concentrated D-psicose solution in a supersaturated state under a metastable zone by adding a D-psicose solution of a concentration lower than that of the solution when D-psicose in the solution is concentrated to a level of supersaturation or higher.

7. The method of claim 1, wherein a supersaturated state under a metastable zone in the crystallizing is present in a range from a saturation concentration to a concentration higher than the saturation concentration by about 6% (g/g solution).

* * * * *